(12) United States Patent
Gillespie

(10) Patent No.: US 6,320,089 B1
(45) Date of Patent: Nov. 20, 2001

(54) PARAFFIN-ISOMERIZATION CATALYST AND PROCESS

(75) Inventor: Ralph D. Gillespie, Gurnee, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/757,059

(22) Filed: Jan. 9, 2001

Related U.S. Application Data

(63) Continuation-in-part of application No. 09/323,341, filed on Jun. 1, 1999, now Pat. No. 6,214,764.

(51) Int. Cl.$^7$ .................. C07C 5/22; C07C 5/21
(52) U.S. Cl. ............ 585/744; 585/734; 585/741; 585/746; 585/747; 585/748; 585/749; 585/750; 585/751
(58) Field of Search ............... 585/734, 741, 585/744, 746, 747, 748, 749, 750, 751

(56) References Cited

U.S. PATENT DOCUMENTS

| | | |
|---|---|---|
| 3,963,643 | 6/1976 | Germanas et al. . |
| 4,032,434 | 6/1977 | Rausch et al. ............... 208/139 |
| 5,607,891 | 3/1997 | Travers et al. ............... 502/229 |
| 5,992,639 | 7/1999 | Alario et al. ............... 502/230 |

*Primary Examiner*—Elizabeth D. Wood
(74) *Attorney, Agent, or Firm*—John G. Tolomei; John P. Spears, Jr.

(57) ABSTRACT

An improved catalyst is disclosed for the conversion of hydrocarbons. The catalyst comprises an alumina support, a Friedel-Crafts metal halide, and a platinum-group metal component, wherein the support comprises primarily eta alumina and a small amount of gamma alumina and has a defined pore-size and acidity characteristics. An isomerization process also is disclosed which is particularly effective for the conversion of $C_4$–$C_7$ alkanes.

5 Claims, 1 Drawing Sheet

PARAFFIN-ISOMERIZATION CATALYST AND PROCESS

CROSS-REFERENCE TO RELATED APPLICATION

This application is a continuation-in-part of application Ser. No. 09/323,341 filed Jun. 1, 1999, which is now U.S. Pat. No. 6,214,764. The teaching of this prior application is incorporated by reference.

BACKGROUND OF THE INVENTION

1. Field of the Invention

This invention relates to an improved catalyst and its use for the conversion of hydrocarbons, particularly for the isomerization of alkanes.

2. General Background

The isomerization of light naphtha is an increasingly important process for the upgrading of petroleum refiners' gasoline pool. The widespread removal of lead antiknock additive from gasoline and the rising demands of high-performance internal-combustion engines are increasing the need for "octane," or knock resistance, in the gasoline pool. In the early years of lead removal, refiners relied principally upon increasing the octane of products from catalytic reforming and fluid catalytic cracking operations. Refiners have largely capitalized on these relatively low-cost upgrading options. More attention has now focused on upgrading the relatively low-octane high-paraffin naphtha component.

There is a long history of catalyst and process technology for the isomerization of light alkanes. The recent expansion of interest, however, has led to significant improvements in this technology. Catalyst and process developments have led to lower operating temperatures, wherein product octane is favored by isomer equilibrium. Substantial reduction in the hydrogen requirement for a stable operation has resulted in a significant cost reduction, principally through elimination of the need for a hydrogen-recycle system. Both of the aforementioned developments have led toward a predominance of liquid in the isomerization reactor feed, in contrast to the vapor-phase operation of the prior art.

Catalysts exhibiting dual hydrogenation-dehydrogenation and cracking functions are applied widely in the petroleum refining and petrochemical industries to the reforming and isomerization of hydrocarbons. Such catalysts generally have the cracking function imparted by an inorganic oxide, zeolite, or halogen, with a platinum-group component usually imparting the hydrogenation-dehydrogenation function. A catalyst useful in isomerization should be formulated to balance its hydrogenation-dehydrogenation and cracking functions to achieve the desired conversion over a prolonged period of time, while effectively utilizing the expensive platinum group metal component.

The performance of a catalyst in isomerization service typically is measured by its activity, selectivity, and stability. Activity refers to the ability of a catalyst to isomerize the reactants into the desired product isomers at a specified set of reaction conditions. Selectivity refers to the proportion of converted feed reacted into the desired product. Stability refers to the rate of change of activity and selectivity during the life of the catalyst. The principal cause of low catalyst stability is the formation of coke, a high-molecular-weight, hydrogen-deficient, carbonaceous material on the catalytic surface. Workers in the isomerization art thus must address the problem of developing catalysts having high activity and stability, and which also either suppress the formation of coke or are not severely affected by the presence of coke.

Catalysts for paraffin isomerization containing a platinum-group metal component and a halide on an alumina support are known in the art. For example, U.S. Pat. No. 3,963,643 (Germanas et al.) teaches a method of manufacturing a catalyst useful in the isomerization of paraffins by compositing a platinum-group metal with gamma or eta alumina and reacting the composite with a Friedel-Crafts metal halide and a polyhalo compound. U.S. Pat. No. 5,607,891 (Travers et al.) teaches a catalyst consisting of chlorine, Group VIII metal, and a support consisting essentially of 85–95% eta alumina and the remainder gamma alumina and its use for benzene reduction and isomerization. However, the art does not suggest a catalyst having the particular characteristics of the present catalyst or the surprising benefits of using this catalyst in the context of modern, primarily liquid-phase, isomerization operations.

The art has attempted to identify characteristics of isomerization catalysts which are important to their performance. For instance, U.S. Pat. No. 4,032,434 issued to R. E. Rausch describes a catalyst in which the desired amounts of halogen is loosely correlated to the catalyst's surface area and tin content.

The catalysts normally comprise an inorganic oxide support, such as alumina. A single type of alumina rather than a mixture is the norm. However, U.S. Pat. No. 5,922,639 issued to F. Alario et al. presents a bifunctional hydrocarbon conversion catalyst, described as a naphtha reforming catalyst, which comprises a mixture of gamma and eta aluminas.

SUMMARY OF THE INVENTION

It is an object of the present invention to provide a novel catalyst useful particularly for the isomerization of isomerizable hydrocarbons. A corollary object of the invention is to provide a process for isomerizing isomerizable hydrocarbons, particularly alkanes having from four to seven carbon atoms per molecule.

This invention is based on the discovery that a catalyst comprising a Friedel-Crafts metal halide and a platinum-group metal on a primarily eta-alumina support having defined critical characteristics demonstrates surprising results in increasing the octane number of $C_5/C_6$ naphtha streams.

A broad embodiment of the present invention is an isomerization catalyst comprising a Friedel-Crafts metal halide and a platinum-group metal component on a principally eta-alumina support which has narrowly defined pore-size and acidity characteristics. Platinum is the preferred platinum-group component and aluminum chloride is the preferred Friedel-Crafts metal halide. The catalyst support preferably comprises eta and gamma alumina in an eta:gamma ratio on a mass basis of from about 4:1 to about 99:1, with the ratio more preferably being at least about 9:1 and optionally at least about 24:1; optimally, the support consists essentially of eta and gamma alumina. A trilobal or triclover extrudate is a preferred shape of the catalyst of the invention.

A preferred catalyst has an average pore diameter of between about 35 and 60 angstroms and a pore-acidity index, defined by measured acidity, pore diameter and surface area, of at least about 7.0.

In another aspect, the invention is a preferred method of preparing the present catalyst by a procedure comprising peptizing an alumina source, forming extrudates from the resulting base material, calcining the extrudates at defined critical conditions, impregnating a platinum-group metal component on the calcined extrudates, oxidizing and reducing the impregnated extrudates and subliming the Friedel-Crafts metal component onto the catalyst.

In yet another aspect, the invention comprises a process for the use of the present catalyst to isomerize isomerizable hydrocarbons. The preferred feedstock comprises $C_4$ to $C_7$ alkanes which are upgraded with respect to their degree of branching and octane number.

These as well as other objects and embodiments will become apparent from the detailed description of the invention.

DESCRIPTION OF THE PREFERRED EMBODIMENTS

Figure 1:
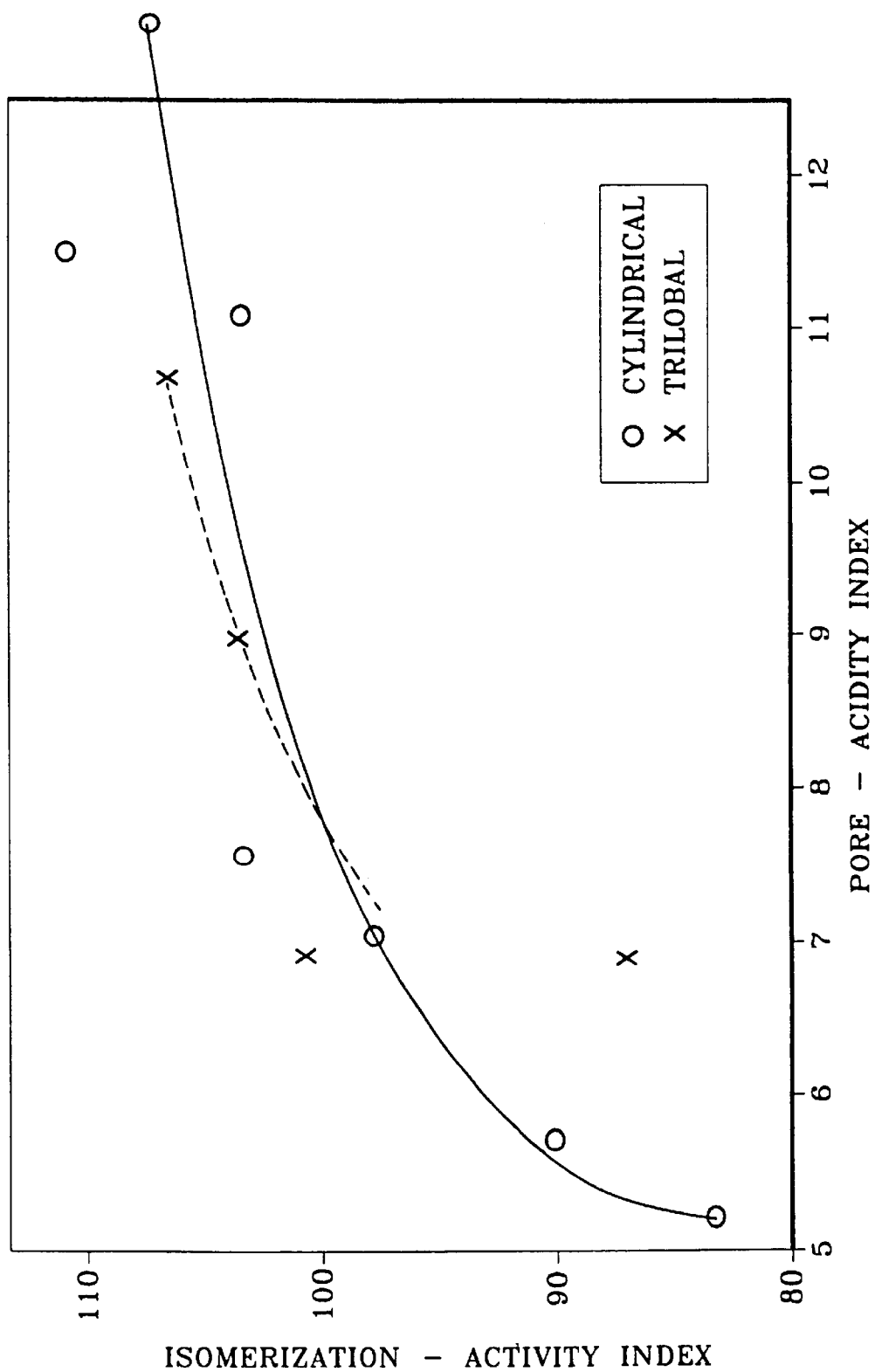
FIG. 1 shows comparative isomerization activity for catalysts of the invention and control catalysts in relation to a pore-acidity index.

The alumina support utilized in the isomerization catalyst of the present invention preferably consists essentially of the crystalline aluminas known as the eta- and gamma-aluminas in a respective ratio of between about 4:1 and about 99:1. The alumina can be formed into any desired shape or type of carrier material known to those skilled in the art such as rods, pills, pellets, tablets, granules, extrudates, and like forms by methods well known to the practitioners of the catalyst material forming art. Spherical carrier particles may be formed, for example, from this alumina by: (1) converting the alumina powder into an alumina sol by reaction with a suitable peptizing acid and water and thereafter dropping a mixture of the resulting sol and a gelling agent into an oil bath to form spherical particles of an alumina gel which are easily converted to a gamma-alumina carrier material by known methods; (2) forming an extrudate from the powder by established methods and thereafter rolling the extrudate particles on a spinning disk until spherical particles are formed which can then be dried and calcined to form the desired particles of spherical carrier material; and (3) wetting the powder with a suitable peptizing agent and thereafter rolling the particles of the powder into spherical masses of the desired size.

A favored form of alumina support is a cylindrical extrudate generally having a diameter of up to about 3.3 mm, with about 0.8 mm being preferred. The length-to-diameter ratio generally is from about 1:1 to 5:1, with about 2:1 usually being optimal. Alternative extrudate forms within the scope of the invention include those with a polylobal or ring cross-section as disclosed in U.S. Pat. No. 4,028,227, incorporated herein by reference; a trilobal cross-section is preferred. Other catalyst forms are described in Fulton, "Selecting the catalyst configuration," Chemical Engineering, May 12, 1986, pp. 97–101, also incorporated by reference. Further extrudate forms within the knowledge of the skilled routineer also may be suitable. Optimally the form of the catalyst will provide a diffusion path, defined as the maximum distance from the external surface to the interior of an extrudate particle, of no more than about 0.3, and preferably no more than about 0.25, times the overall diameter of the particle. The overall diameter is defined as the diameter of a circle circumscribed around the cross section of the particle.

An eta-rich alumina support is produced from a suitable alumina base material by the dehydroxylation of one or more base, material preferably rich in bayerite, nordstrandite and gibbsite. The ratio of eta:gamma ratio in the finished catalyst preferably is from about 4:1 to about 99:1, and more preferably at least about 9:1; optionally the ratio is between about 24:1 and about 99:1 LaRoche Versal B is one example of a suitable alumina source. The extrudate particle form of the carrier material may be prepared by mixing alumina powder with water and suitable peptizing agents such as nitric acid, acetic acid, aluminum nitrate, and the like material until an extrudable dough is formed. The amount of water added to form the dough is typically sufficient to give a Loss on Ignition (LOI) at 500° C. of about 30 to 65 mass %, with a value of about 35 to about 45 mass % being especially preferred. The acid addition is generally sufficient to provide 2 to 7 mass % of the volatile-free alumina powder used in the mix, with a value of 3 to 4 mass % being especially preferred. Preferably from about 0.1 to about 10 mass-% of an extrusion aid such as Methocel, and more preferably from about 1 to about 5 mass-%, is included in the mix. The resulting dough optimally is then mulled and extruded through a suitably sized die to form extrudate particles as described hereinabove.

The extrudate particles are dried at a temperature of about 150° to about 200° C., and then calcined at a temperature of about 500° to about 650° C. for a period of 0.2 to 10 hours to create the preferred form of the refractory inorganic oxide catalyst base. In order to obtain the distinctive properties of the present catalyst, the calcination preferably is effected within a critical temperature range of from of about 545° to about 610° C., and more preferably from about 560° to about 580° C. Calcination conditions are established to provide a finished-catalyst surface area of about 160 to 250 $m^2/g$ (preferably no more than about 230 $m^2/g$) with an average pore diameter of from about 35 to about 60 angstroms.

An essential ingredient of the catalyst is the platinum-group metal component. Of the platinum group, i.e., platinum, palladium, rhodium, ruthenium, osmium and iridium, palladium is a preferred component and platinum is especially preferred. Mixtures of platinum-group metals also are within the scope of this invention. This component may exist within the final catalytic composite as a compound such as an oxide, sulfide, halide, or oxyhalide, in chemical combination with one or more of the other ingredients of the composite, or as an elemental metal. Best results are obtained when substantially all of this component is present in the elemental state. This component may be present in the final catalyst composite in any amount which is catalytically effective, but relatively small amounts are preferred. In fact, the surface-layer platinum-group metal component generally will comprise about 0.01 to 2 mass % of the final catalyst, calculated on an elemental basis. Excellent results are obtained when the catalyst contains about 0.05 to 1 mass % of platinum.

Typical platinum-group compounds which may be employed in preparing the catalyst of the invention are chloroplatinic acid, ammonium chloroplatinate, bromoplatinic acid, platinum dichloride, platinum tetrachloride hydrate, platinum dichlorocarbonyl dichloride, dinitrodiaminoplatinum, palladium chloride, palladium chloride dihydrate, palladium nitrate, etc. Chloroplatinic acid is preferred as a source of the especially preferred platinum component. A surface-layer platinum component may be impregnated onto the catalyst from a solution of chloroplatinic acid in the absence of strong mineral acids such as hydrochloric and nitric acid.

An optional embodiment of the catalyst of the present invention is that the platinum-group metal component is concentrated in the surface layer of each catalyst particle. In defining the present invention, a "surface-layer" component has a concentration in the micron surface layer of the catalyst particle that is at least 1.5 times the concentration in the central core of the catalyst particle. Preferably, the surface-layer concentration of platinum-group metal is at least about twice the concentration in the central core. As exemplified hereinbelow, the surface layer may be 100 or 150 microns deep and the central core may be 50% of the volume or 50% of the diameter of the particle; however, other quantitative criteria are not excluded thereby. Further details of the characteristics and preparation of a surface-layer platinum-group metal component are contained in U.S. Pat. No. 5,004,859 (Schmidt et al.), incorporated herein by reference.

It is within the scope of the present invention that the catalyst may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art. Preferably, however, the catalyst consists essentially of the alumina support, platinum-group metal component, and a Friedel-Crafts metal halide. This preferred formulation is free of modifier metals, such as tin or indium or halogen other than in the Friedel-Crafts metal halide.

The composite, before addition to the Friedel-Crafts metal halide, is dried and calcined. The drying is carried out at a temperature of about 100° to 300°, followed by calcination or oxidation at a temperature of from about 375° to 600° C. in an air or oxygen atmosphere for a period of about 0.5 to 10 hours in order to convert the metallic components substantially to the oxide form.

Another essential component of the catalyst of the present invention is a Friedel-Crafts metal halide. Suitable metal halides of the Friedel-Crafts type include aluminum chloride, aluminum bromide, ferric chloride, ferric bromide, zinc chloride and the like compounds, with the aluminum halides and particularly aluminum chloride ordinarily yielding best results. Generally, this component can be incorporated into the catalyst of the present invention by way of the conventional methods for adding metallic halides of this type; however, best results are ordinarily obtained when the metallic halide is sublimed onto the surface of the support according to the preferred method disclosed in U.S. Pat. No. 2,999,074, which is incorporated by reference.

In the preferred method, wherein the calcined refractory inorganic-oxide support is impregnated with a Friedel-Crafts metal halide component, the presence of chemically combined hydroxyl groups in the refractory inorganic oxide allows a reaction to occur between the Friedel-Crafts metal halide and the hydroxyl group of the support. For example, aluminum chloride reacts with the hydroxyl groups in the preferred alumina support to yield Al—O—AlCl$_2$ active centers which enhance the catalytic behavior of the catalyst. Since chloride ions and hydroxyl ions occupy similar sites on the support, more hydroxyl sites will be available for possible interaction with the Friedel-Crafts metal halide when the chloride population of the sites is low. Therefore, potentially more active Friedel-Crafts type versions of the catalyst will be obtained when the chloride content of the support is in the low range of the 0.1 to 10 mass-% range.

The Friedel-Crafts metal halide may be impregnated onto the catalyst by sublimation of the Friedel-Crafts metal halide onto the calcined support under conditions to combine the sublimed Friedel-Crafts metal halide with the hydroxyl groups of the calcined support. This reaction is typically accompanied by the elimination of about 0.5 to about 2.0 moles of hydrogen chloride per mole of Friedel-Crafts metal halide reacted with the inorganic-oxide support. In subliming aluminum chloride, which sublimes at about 184° C., suitable impregnation temperatures range from about 190° C. to 700° C., with a preferable range being from about 200° C. to 600° C. The sublimation can be conducted at atmospheric pressure or under increased pressure and in the presence of absence of diluent gases such a hydrogen or light paraffinic hydrocarbons or both. The impregnation of the Friedel-Crafts metal halide may be conducted batch-wise, but a preferred method for impregnating the calcined support is to pass sublimed AlCl$_3$ vapors, in admixture with a carrier gas such as hydrogen, through a calcined catalyst bed. This method both continuously deposits and reacts the aluminum chloride and also removes the evolved HCl.

The amount of Friedel-Crafts metal halide combined with the calcined may range from about 1 up to 15 mass % to the Friedel-Crafts metal-halide-free, calcined composite. The final composite containing the sublimed Friedel-Crafts metal halide is treated to remove the unreacted Friedel-Crafts metal halide by subjecting the composite to a temperature above the sublimation temperature of the Friedel-Crafts metal halide for a time sufficient to remove from the composite any unreacted Friedel-Crafts metal halide. In the case of AlCl$_3$, temperatures of about 400° C. to 600° C. and times of from about 1 to 48 hours are sufficient.

In a preferred embodiment of the present invention, the resultant oxidized catalytic composite is subjected to a substantially water-free and hydrocarbon-free reduction step prior to its use in the conversion of hydrocarbons. This step is designed to selectively reduce the platinum-group metal component to the corresponding elemental metal and to insure a finely divided dispersion of the metal component throughout the carrier material. Preferably substantially pure and dry hydrogen (i.e., less than 20 vol. ppm H$_2$O) is used as the reducing agent in this step. The reducing agent is contacted with the oxidized composite at conditions including a temperature of about 425° C. to about 650° C. and a period of time of about 0.5 to 2 hours to reduce substantially all of the platinum-group component to its elemental metallic state. This reduction treatment may be performed in situ as part of a start-up sequence if precautions are taken to predry the plant to a substantially water-free state and if substantially water-free and hydrocarbon-free hydrogen is used. Contact with water in general is to be avoided as water will deactivate the catalyst. Thus, both catalyst treatment and operation should be substantially water free.

The catalyst of the present invention may contain an additional halogen component. The halogen component may be either fluorine, chlorine, bromine or iodine or mixtures thereof or an organic polyhalo component. Chlorine is the preferred halogen component. The halogen component is generally present in a combined state with the inorganic-oxide support. Although not essential to the invention, the halogen component is preferably well dispersed throughout the catalyst. The halogen component may comprise from more than 0.2 to about 15 mass-%, calculated on an elemental basis, of the final catalyst. Further details of halogen components and their incorporation into the catalyst are disclosed in U.S. Pat. No. 5,004,859 referenced above.

The finished catalyst has a surface area of about 160 to about 250 m$^2$/g (preferably no more than about 230 m$^2$/g) with an average pore diameter of from about 35 to about 60 angstroms. A catalyst of the invention also is characterized by a pore-acidity index, calculated as $100 \times (^{PD \times Acidity}/SA)$ wherein PD=average pore diameter in angstroms; Acidity= mmols TMP/g @ 120° C. and SA=surface area in m²/g. Catalysts of the invention have a pore-acidity index of at least about 7.0. It is believed, without so limiting the invention, that mass-transfer and reaction-kinetics rates are balanced at these values and effect superior isomerization selectivity with high activity.

Surface area is measured using nitrogen by the well known BET (Brunauer-Emmett-Teller) method, which also indicates average pore diameter. Acidity is measured by loading the sample as powder in a glass tube and pretreating under high vacuum (ca. $10^{-6}$ torr) at 600° C. for 2 hours. The samples are then cooled to 120° C. and exposed to trimethylphosphine (TMP) for 15 minutes followed by a 45-minute equilibration time, and then degassed with high vacuum. The TMP exposed to the sample is stored in a known volume of gas line and is exposed to the sample by opening a valve connecting this line to sample chamber. The amount of adsorbed TMP is calculated from the vapor-pressure drop caused by adsorption on the sample from the known volume of the gas line, compared to the change in vapor pressure with no sample present.

In the process of the present invention, an isomerizable hydrocarbon feedstock, preferably in admixture with hydrogen, contacts a catalyst of the type hereinbefore described in a hydrocarbon-isomerization zone to obtain an isoparaffin-rich product. Contacting may be effected using the catalyst in a fixed-bed system, a moving-bed system, a fluidized-bed system, or in a batch-type operation. In view of the danger of attrition loss of the valuable catalyst and of operational advantages, it is preferred to use a fixed-bed system. In this system, a hydrogen-rich gas and the charge stock are preheated by suitable heating means to the desired reaction temperature and then passed into an isomerization zone containing a fixed bed of the catalyst as previously characterized. The isomerization zone may be in a single reactor or in two or more separate reactors with suitable means therebetween to insure that the desired isomerization temperature is maintained at the entrance to each zone. Two or more reactors in sequence are preferred to enable improved isomerization through control of individual reactor temperatures and for partial catalyst replacement without a process shutdown. The reactants may be contacted with the catalyst in either upward, downward, or radial flow fashion. The reactants may be in the liquid phase, a mixed liquid-vapor phase, or a vapor phase when contacted with the catalyst, with excellent results being obtained by application of the present invention to a primarily liquid-phase operation.

In the group of isomerizable hydrocarbons suitable as feedstock to the process of the present invention, alkanes having from 4 to 7 carbon atoms per molecule ($C_4$–$C_7$) are preferred. These may be contained in such streams from petroleum refining or synthetic-fuel production as light straight-run naphtha, light natural gasoline, light reformate, light raffinate from aromatics extraction, light cracked naphtha, normal-butane concentrate, field butanes and the like. An especially preferred feedstock is light straight-run naphtha, containing more than 50% of $C_5$ and $C_6$ paraffins with a high concentration of low-octane normal paraffins; this feedstock is particularly susceptible to octane-number upgrading by isomerization. The light straight-run naphtha and other feedstocks also may contain naphthenes, aromatics, olefins, and hydrocarbons heavier than $C_6$. The olefin content should be limited to a maximum of 10% and the content of hydrocarbons heavier than $C_6$ to 20% for effective control of hydrogen consumption, cracking reactions, heat of reaction and catalyst activity.

It is generally known that high-chloride platinum-alumina catalysts of this type are highly sensitive to sulfur- and oxygen-containing compounds. The feedstock therefore must be relatively free of such compounds, with a sulfur concentration generally no greater than 0.5 ppm. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high-activity chloride from the catalyst and replacing it with inactive aluminum hydroxide. Therefore, water and oxygenates that can decompose to form water can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. Adsorption systems for the removal of sulfur and water from hydrocarbon streams are well known to those skilled in the art.

Hydrogen is admixed with the isomerizable hydrocarbon feed to provide a mole ratio of hydrogen to hydrocarbon feed of about 0.01 to 5. The hydrogen may be supplied totally from outside the process or supplemented by hydrogen recycled to the feed after separation from reactor effluent. Light hydrocarbons and small amounts of inerts such as nitrogen and argon may be present in the hydrogen. Water should be removed from hydrogen supplied from outside the process, preferably by an adsorption system as is known in the art.

Although there is no net consumption of hydrogen in the isomerization reaction, hydrogen generally will be consumed in a number of side reactions such as cracking, disproportionation, and aromatics and olefin saturation. Such hydrogen consumption typically will be in a mol ratio to the hydrocarbon feed of about 0.03 to 0.1. Hydrogen in excess of consumption requirements is maintained in the reaction zone to enhance catalyst stability and maintain conversion by compensation for variations in feed composition, as well as to suppress the formation of carbonaceous compounds, usually referred to as coke, which foul the catalyst.

In a preferred embodiment, the hydrogen to hydrocarbon mol ratio in the reactor effluent is equal to or less than 0.05. Generally, a mol ratio of 0.05 or less obviates the need to recycle hydrogen from the reactor effluent to the feed. It has been found that the amount of hydrogen needed for suppressing coke formation need not exceed dissolved hydrogen levels. The amount of hydrogen in solution at the normal conditions of the reactor effluent will usually be in a ratio of from about 0.02 to less 0.01. The amount of excess hydrogen over consumption requirements that is required for good stability and conversion is in a ratio of hydrogen to hydrocarbons of from 0.01 to less than 0.05 as measured at the effluent of the isomerization zone. Adding the dissolved and excess hydrogen proportions show that the 0.05 hydrogen to hydrocarbon ratio at the effluent will satisfy these requirements for most feeds. The catalyst of the present invention show excellent results in a primarily liquid-phase process operation with reactor-effluent hydrogen-to-hydrocarbon mol ratios of 0.05 or less.

Isomerization conditions usually comprise temperatures ranging from about 40° to 250° C. Lower reaction temperatures are generally preferred since the equilibrium directionally favors higher concentrations of isoalkanes relative to normal alkanes. Lower temperatures are particularly useful in processing feeds composed of $C_5$ and $C_6$ alkanes, as lower temperatures favor equilibrium mixtures having the highest concentration of high-octane highly branched isopentane and isohexanes. When the feed mixture is primarily $C_5$ and $C_6$ alkanes, temperatures in the range of from about 40° to about 160° C. are preferred. When it is desired to isomerize significant amounts of butanes, higher reaction temperatures in the range from about 145° to 225° C. are required to maintain catalyst activity.

Operating pressures generally range from about 100 kPa to 10 MPa absolute, with preferred pressures in the range of from 2 to 3.5 MPa. Liquid hourly space velocities range from about 0.25 to about 12 liquid volumes of isomerizable hydrocarbon feed per hour per volume of catalyst, with a range of about 0.5 to 5 $hr^{-1}$ being preferred.

The isomerization process generally also requires the presence of a small amount of an organic chloride promoter. The organic chloride promoter serves to maintain a high level of active chloride on the catalyst, as low levels are continuously stripped off the catalyst by the hydrocarbon feed. The concentration of promoter in the combined feed preferably is maintained at from 30 to 300 mass ppm. The preferred promoter compound is carbon tetrachloride. Other suitable promoter compounds include oxygen-free decomposable organic chlorides such as propyldichloride, butylchloride, and chloroform, to name only a few of such compounds. The need to keep the reactants dry is reinforced by the presence of the organic chloride compound which may convert, in part, to hydrogen chloride. As long as the hydrocarbon feed and hydrogen are dried as described hereinabove, there will be no adverse effect from the presence of small amounts of hydrogen chloride.

The isomerization product from the especially preferred light-naphtha feedstock will contain some low-octane normal paraffins and intermediate- octane methylhexanes as well as the desired highest-octane isopentane and dimethylbutane. It is within the scope of the present invention that the liquid product from the process is subjected to separation steps to recycle the lower- octane portion of this product to the isomerization reaction and to recover an isoparaffin concentrate as a net product. Generally, low-octane normal paraffins are separated and recycled to upgrade the octane number of the net product. Less-branched $C_6$ and $C_7$ paraffins also may be separated and recycled, along with lesser amounts of hydrocarbons which are difficult to separate from the recycled hydrocarbons. Techniques to achieve this separation are well known in the art, and include fractionation and molecular-sieve adsorption.

Preferably part or all of the isoparaffin-rich product and/or the isoparaffin concentrate are blended into finished gasoline along with other gasoline components from refinery processing including but not limited to one or more of butanes, butenes, pentanes, naphtha, catalytic reformate, isomerate, alkylate, polymer, aromatic extract, heavy aromatics; gasoline from catalytic cracking, hydrocracking, thermal cracking, thermal reforming, steam pyrolysis and coking; oxygenates such as methanol, ethanol, propanol, isopropanol, TBA, SBA, MTBE, ETBE, MTAE and higher alcohols and ethers; and small amounts of additives to promote gasoline stability and uniformity, avoid corrosion and weather problems, maintain a clean engine and improve driveability.

EXAMPLES

The following examples are presented to elucidate the catalyst and process of the present invention. These examples are offered as illustrative embodiments and should not be interpreted as limiting the claims.

Example I

Two control catalysts of the known art were prepared in order to demonstrate the advantages of the present catalyst.

An extruded gamma alumina base of the known art, having a particle diameter of about 800 microns, was divided into two portions. Both were vacuum-impregnated in a solution of 3.5 mass % chloroplatinic acid, 2 mass % hydrochloric acid, and 3.5% mass % nitric acid in a volume ratio of 9 parts solution to 10 parts base to obtain peptized base material having a platinum to base ratio of approximately 0.9. The resulting mixture was cold-rolled for approximately 1 hour and evaporated until dry. The composites then were oxidized and the chloride content adjusted by contact with a 1 M hydrochloric acid solution at 525° C. at a rate of 45 cc/hour for 2 hours. The composites then were reduced in electrolytic hydrogen at 565° C. for approximately 2 hours and found to contain approximately 0.25 mass-% Pt and approximately 1 mass-% chloride. Impregnation of active chloride to a level of approximately 7 mass-% was accomplished by sublimating aluminum chloride with hydrogen and contacting the catalysts with the sublimated aluminum chloride for approximately 45 minutes at 550° C.

These catalysts were designated "Catalyst X" and "Catalyst Y" and had the following characteristics (%=mass-%; SA=surface area; PD=pore diameter in angstroms; Acidity= mmols TMP/g @ 120° C.):

| Catalyst | Pt, % | Cl, % | SA, $m^2/g$ | PD, Å | Acidity |
|---|---|---|---|---|---|
| X | 0.249 | 6.29 | 191.6 | 83 | 0.367 |
| Y | 0.255 | 7.45 | 193.6 | 96 | 0.345 |

Example II

To illustrate the invention, catalysts were prepared from a bayerite alumina source; the following description applies to Catalyst "A." LaRoche Versal B alumina in an amount of 2000 grams was placed in a muller. The muller was started and 103.2 grams of 70.7% nitric acid and 268 grams of deionized water were added over a 5-minute period, followed by mixing for 20 minutes. Methocel in an amount of 33.15 grams was added, and mulling was continued for 10 minutes. The mulled mixture then was extruded with a Bonnot extruder using a die plate with 1/32" circular holes to produce cylindrical extrudates. The extrudates were dried for 2 hours at 100° C., heated to 260° C. in 10% moisture, and finally calcined at 575° C. in 5 mole % moisture for 30 minutes.

The extrudates were washed with a 1 mass-% ammonium nitrate to achieve a sodium level of less than 100 parts per million (ppm Na), dried for 2 hours at 100° C., heated to 205° C., and calcined at 325° C. The washed extrudates then were impregnated in a solution of 3.5 mass % chloroplatinic acid, 2 mass % hydrochloric acid, and 3.5% mass % nitric acid in a volume ratio of 9 parts solution to 10 parts base to obtain peptized base material having a platinum to base ratio of approximately 0.9. The resulting mixture was cold-rolled for approximately 1 hour and evaporated until dry. The composites then were oxidized at 475° C. for 2 hours and reduced in electrolytic hydrogen at 500° C. for approximately 2 hours, and found to contain approximately 0.25 mass-% Pt and approximately 1 mass-% chloride. The chloride content was adjusted by contact with anhydrous HCl. Impregnation of active chloride to a level of approximately 6–8 mass-% was accomplished by sublimating aluminum chloride with hydrogen and contacting the catalysts with the sublimated aluminum chloride for approximately 25 minutes at 470° C. followed by treatment with anhydrous HCl at 260° C.

The catalysts prepared in this manner were designated as Catalysts A through H, differing in methylcellulose addition (A: 2.5 mass-%; B,E–G: 5 mass-%; C,D,H: 0 mass-%) and base calcination temperature as indicated below. The catalysts had the following characteristics (Calc.T=base calcination temperature, ° C.; %=mass-%; SA=surface area; PD=pore diameter in angstroms; Acidity=mmols TMP/g @ 120° C.):

| Catalyst | Calc. T | Pt, % | Cl, % | SA, m²/g | PD, Å | Acidity |
|---|---|---|---|---|---|---|
| A | 575 | 0.275 | 6.7 | 200.8 | 47 | 0.49 |
| B | 600 | 0.265 | 6.54 | 183 | 53 | 0.384 |
| C | 600 | 0.27 | 6.92 | 198 | 45 | 0.333 |
| D | 650 | 0.273 | 5.67 | 165 | 56 | 0.384 |
| E | 550 | 0.269 | 7.43 | 219.2 | 44 | 0.351 |
| F | 650 | 0.263 | 5.93 | 160.2 | 63 | 0.304 |
| G | 500 | 0.274 | 8.41 | 254.2 | 36 | 0.404 |
| H | 500 | 0.274 | 8.31 | 255 | 32 | 0.412 |

Example III

A pore-acidity index was calculated for each of the catalysts A–H. As defined hereinabove, this index is characterized as $100 \times (^{PD \times Acidity}/SA)$ or: 100×(pore diameter, angstroms)×(acidity, mmols TMP/g@ 120° C.)/(surface area, m²/g). The results are as follows:

| Catalyst | Index |
|---|---|
| A | 11.5 |
| B | 11.1 |
| C | 7.6 |
| D | 13.0 |
| E | 7.05 |
| F | 12.0 |
| G | 5.7 |
| H | 5.2 |

Catalysts A–D met the criteria of the invention, as did Catalyst E on a marginal basis. Catalyst F failed on the basis of surface area. The relative isomerization activity of the above catalysts is disclosed in FIG. 1 as discussed hereinafter.

Example IV

Additional catalysts with a composition as disclosed in Example II, but with a different extrudate cross section, were prepared to illustrate the invention. The preparation steps followed those described in Example II except that the mulled mixture was extruded with a trilobal or triclover-form die as illustrated in FIG. 2 and the washing step was not needed to obtain a content of less than 100 ppm Na.

The catalysts prepared in this manner were designated as Catalysts J through M, differing in base calcination temperature as indicated below. The catalysts had the following characteristics (Calc.T=base calcination temperature, ° C.; %=mass-%; SA=surface area; PD=pore diameter in angstroms; Acidity=mmols TMP/g@ 120° C.):

| Catalyst | Calc. T | Pt, % | Cl, % | SA, m²/g | PD, Å | Acidity |
|---|---|---|---|---|---|---|
| J | 580 | 0.26 | 7.9 | 198 | 54 | 0.395 |
| K | 560 | 0.23 | 7.4 | 218 | 46 | 0.427 |
| L | 540 | 0.26 | 7.0 | 248 | 40 | 0.428 |
| M | 560 | 0.25 | 7.4 | 213 | 46 | 0.318 |

Example V

A pore-acidity index was calculated for each of the catalysts J–M. As defined hereinabove, this index is calculated as $100 \times (^{PD \times Acidity}/SA)$. The results are as follows:

| Catalyst | Index |
|---|---|
| J | 10.7 |
| K | 9.0 |
| L | 6.9 |
| M | 6.9 |

Example VI

Catalysts A through H and J through M were tested for relative performance in isomerization service. The same feedstock was used for each of the catalyst tests, and was a blend of $C_5$ and $C_6$ hydrocarbons having the following composition in mass %:

| | |
|---|---|
| n-Pentane | 43 |
| n-Hexane | 47 |
| Methylcyclopentane + cyclohexane | 8 |
| n-Heptane | 2 |
| Total | 100 |

Once-through isomerization tests were performed at 450 psig, a temperature of 116° C., 3.4 mass hourly space velocity, and 0.3 hydrogen to hydrocarbon mol ratio.

The results are expressed below as percentages of isopentane to total pentanes ("$iC_5/C_5$") and 2,2-dimethylbutane to total hexanes ("2,2-DMB") in the product. These percentages are more sensitive tests of catalyst performance than octane-number measurements, showing the concentration of the highest-octane isopentane and dimethylbutane isomers in the product with a high degree of precision in contrast to the low reproducibility of the measurement of product octane.

In addition, an isomerization-activity index ("Activity") is shown to equalize the weighting of catalyst-performance results on pentanes and hexanes, corresponding to [($iC_5/C_5$)+4×(2,2-DMB)]. Isomerization-activity indices of about 100 or more indicate an effective catalyst. The results are shown in FIG. 1 in comparison to the control catalysts as a plot of the isomerization-activity index vs. pore-acidity index:

| Catalyst | iC$_5$/C$_5$ | 2,2-DMB | Activity |
|---|---|---|---|
| A | 56.83 | 13.53 | 111.0 |
| B | 53.86 | 12.36 | 103.3 |
| C | 53.53 | 12.46 | 103.4 |
| D | 55.46 | 12.93 | 107.2 |
| E | 50.95 | 11.84 | 98.3 |
| F | 50.62 | 11.03 | 94.7 |
| G | 47.41 | 10.69 | 90.2 |
| J | 54.3 | 13.1 | 106.7 |
| K | 52.9 | 12.7 | 103.7 |
| L | 50.9 | 12.5 | 100.9 |
| M | 45.4 | 10.4 | 87.0 |

I claim:

1. A process for isomerizing isomerizable hydrocarbons which comprises contacting an isomerizable hydrocarbon feedstock with an isomerization catalyst having an average pore diameter of from about 35 to about 60 angstroms and a pore-acidity index of at least about 7.0 and comprising an alumina support consisting essentially of eta and gamma alumina in an eta:gamma ratio on a mass basis of from about 4:1 to about 99:1, from about 1 to 15 mass % of a Friedel-Crafts metal halide and from about 0.01 to 2 mass % on an elemental basis of a platinum-group metal component in a hydrocarbon-isomerization zone at isomerization conditions including the presence of added chloride promoter to obtain an isoparaffin-containing product.

2. The process of claim 1 wherein the isomerization conditions comprise a temperature of about 40° to 250° C., a pressure of about 100 kPa to 10 MPa, a liquid hourly space velocity of about 0.5 to about 5 liquid volumes per hour of isomerizable hydrocarbons per volume of catalyst, and a mole ratio of hydrogen to isomerizable hydrocarbon feed of about 0.01 to 5.

3. The process of claim 2 wherein the temperature is about 40° to about 160° C.

4. The process of claim 3 wherein the mole ratio of hydrogen to hydrocarbons in the process reactor effluent is less than about 0.05 to 1.0.

5. The process of claim 2 wherein the eta:gamma ratio of the alumina support is at least about 9:1.

* * * * *